(12) United States Patent
Boussignac

(10) Patent No.: US 10,195,382 B2
(45) Date of Patent: Feb. 5, 2019

(54) ARTIFICIAL RESPIRATION DEVICE FOR RESUSCITATING A PERSON IN A STATE OF CARDIAC ARREST

(76) Inventor: Georges Boussignac, Antony (FR)

( * ) Notice: Subject to any disclaimer, the term of this patent is extended or adjusted under 35 U.S.C. 154(b) by 455 days.

(21) Appl. No.: 13/979,712

(22) PCT Filed: Jan. 20, 2012

(86) PCT No.: PCT/FR2012/050124
§ 371 (c)(1),
(2), (4) Date: Jul. 15, 2013

(87) PCT Pub. No.: WO2012/104517
PCT Pub. Date: Aug. 9, 2012

(65) Prior Publication Data
US 2013/0291868 A1  Nov. 7, 2013

(30) Foreign Application Priority Data
Feb. 3, 2011  (FR) ..................... 11 00338

(51) Int. Cl.
| | |
|---|---|
| *A61M 16/04* | (2006.01) |
| *A61M 16/06* | (2006.01) |
| *A61M 16/12* | (2006.01) |
| *A61M 16/08* | (2006.01) |
| *A61M 16/00* | (2006.01) |

(52) U.S. Cl.
CPC .......... *A61M 16/044* (2013.01); *A61M 16/04* (2013.01); *A61M 16/0409* (2014.02); *A61M 16/06* (2013.01); *A61M 16/085* (2014.02); *A61M 16/0858* (2014.02); *A61M 16/0866* (2014.02); *A61M 16/12* (2013.01); *A61M 16/127* (2014.02); *A61M 2016/0027* (2013.01)

(58) Field of Classification Search
CPC .............. A61M 16/044; A61M 16/127; A61M 16/0409; A61M 16/085; A61M 16/0858; A61M 16/0866; A61M 16/04; A61M 16/06; A61M 16/12; A61M 16/0875; A61M 2016/0027
See application file for complete search history.

(56) References Cited

U.S. PATENT DOCUMENTS

| | | |
|---|---|---|
| 5,538,002 A | 7/1996 | Boussignac et al. |
| 5,551,420 A | 9/1996 | Lurie et al. |
| (Continued) | | |

FOREIGN PATENT DOCUMENTS

| | | |
|---|---|---|
| EP | 0 701 834 A1 | 3/1996 |
| EP | 0 911 051 A1 | 4/1999 |
| (Continued) | | |

OTHER PUBLICATIONS

International Search Report, dated Mar. 28, 2012, from corresponding PCT application.

*Primary Examiner* — Gregory Anderson
*Assistant Examiner* — Victoria Murphy
(74) *Attorney, Agent, or Firm* — Young & Thompson

(57) ABSTRACT

An artificial respiration device for resuscitating a person in a state of cardiac arrest is provided that includes a tubular element, auxiliary channels continuously injecting jets of breathing gas, a deflection element that forces the jets of breathing gas to converge inside the tubular element, and a local restriction of the internal cross-section of the tubular element.

8 Claims, 3 Drawing Sheets

(56) References Cited

U.S. PATENT DOCUMENTS

| | | |
|---|---|---|
| 6,152,132 A | 11/2000 | Psaros |
| 6,273,087 B1 | 8/2001 | Boussignac et al. |
| 2008/0245368 A1 | 10/2008 | Dunsmore et al. |
| 2010/0218769 A1 | 9/2010 | Boussignac |
| 2010/0229865 A1* | 9/2010 | Boussignac ........... A61M 16/04 128/205.24 |
| 2010/0282262 A1 | 11/2010 | Boussignac |

FOREIGN PATENT DOCUMENTS

| | | |
|---|---|---|
| EP | 2 228 088 A1 | 9/2010 |
| FR | 2 911 073 A1 | 7/2008 |
| FR | 2 912 660 A1 | 8/2008 |
| FR | 2 921 840 A1 | 4/2009 |
| JP | H11-137690 | 5/1999 |
| JP | 2010-523220 | 7/2010 |

\* cited by examiner

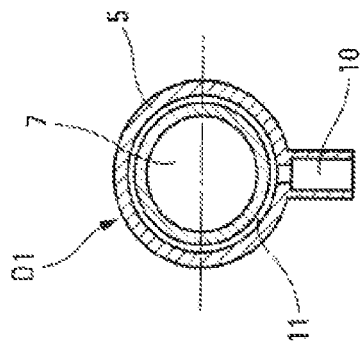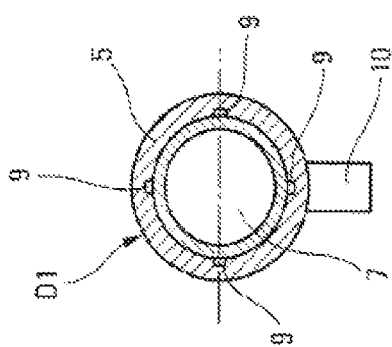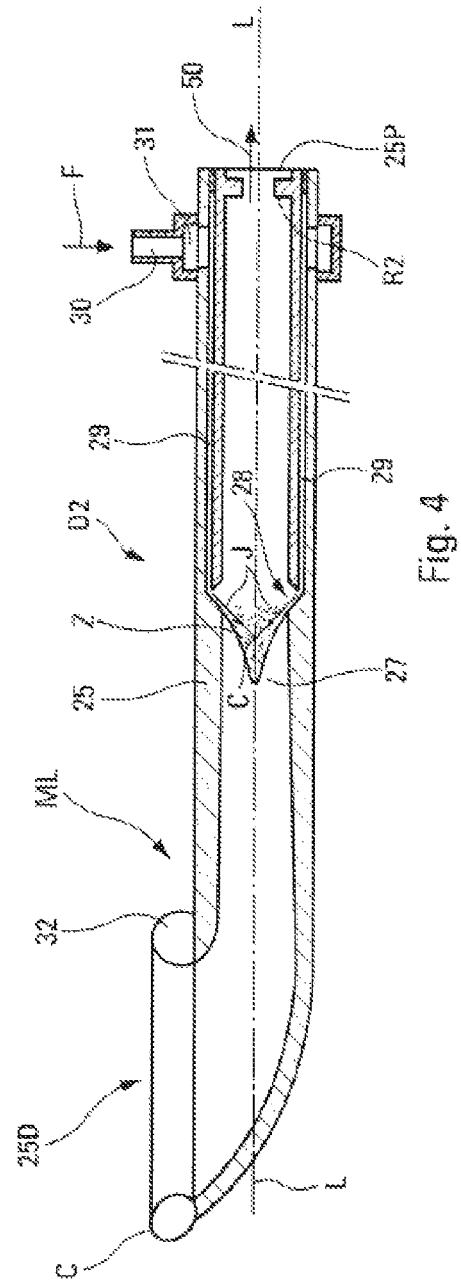

ARTIFICIAL RESPIRATION DEVICE FOR RESUSCITATING A PERSON IN A STATE OF CARDIAC ARREST

BACKGROUND OF THE INVENTION

Field of the Invention

The invention relates to an artificial respiration device that can be used during the resuscitation of persons in state of cardiac arrest.

Description of the Related Art

It is known that, to try to resuscitate a person in state of cardiac arrest, alternated phased compressions and decompressions are exerted on the thoracic cage of this person, tending to restore the expiration and inspiration movements, as well as the blood circulation.

Moreover, it is already know, by the European application EP-0911051 (property of the Applicant), an artificial respiration device for persons in state of cardiac arrest and under resuscitation by alternated compressions and decompressions of their thoracic cage. Such a known artificial respiration device includes:

- a tubular element that forms a main channel and that is intended to be connected by its distal end to a respiratory tract of a person, whereas the proximal end of said tubular element is external to said person and the respiratory system of the latter is connected to the outside through said main channel;
- peripheral auxiliary channels than open out into said main channel, said auxiliary channels being continuously supplied with respiratory gas; and
- deflection means, for making converge toward each other, inside said main channel, the jets of respiratory gas continuously injected by said auxiliary channels.

Hence, the patient is continuously ventilated by said jets of respiratory gas.

The applicant has found that this respiratory assistance device for patients in spontaneous respiration may be successfully used as an artificial respiration device (and no longer only as a respiratory assistance device) in persons in state of cardiac arrest and under resuscitation by alternated compressions and decompressions of their thoracic cage, the jets of said respiratory gas favoring the recovery of inspiration and blood circulation.

However, the Applicant has noticed that said respiratory gas, continuously introduced into the lungs of the person in state of cardiac arrest, generates in these latter, at the end of a compression and at the beginning of the subsequent decompression, a positive residual pressure, which lasts for a part of said decompression, before disappearing and being replaced by a negative pressure generated by the decompression. Such a positive residual pressure, on the one hand, forms an obstacle to external air intake through said tubular element, and on the other hand, is kept up by said intake external air. The result is that, during a significant part of each decompression, the lungs of the person badly intake the external air and blood circulation (in particular the venous return) is not satisfactorily ensured at the ends (head, arms, legs) of the person.

BRIEF SUMMARY OF THE INVENTION

The present invention has for object to remedy this drawback.

For that purpose, according to the invention, the above-described artificial respiration device, which is particularly intended for the resuscitation of a person in cardiac arrest, in which an oblong-shaped pressure area originates at the distal end of said auxiliary channels and elongates in the distal direction, along the longitudinal axis of said main channel, is remarkable:

- in that it includes at least one permanent local section narrowing, of constant shape and arrangement, so as to form a local resistance on the gas flow through said main channel, whatever the flow direction thereof; and
- in that said local narrowing, which is in the form of a protruding internal ring, is longitudinally remote from and external to said oblong pressure area.

Hence, thanks to the invention, during a compression of the thoracic cage of the person under resuscitation, the local resistance, appearing at said narrowing and being exerted on the gas flow through the main channel, generates an increase of pressure (positive pressure) inside the lungs, the air expelled from said lungs escaping freely but with more difficulty than in the absence of a local narrowing.

Conversely, during a decompression, the pressure decreases more (negative pressure) in the lungs than with a known artificial respiration device devoid of local narrowing. The external air entry slow-down, generated by said narrowing, allows a progressive and controlled intake of the external air toward the lungs of the person, which leads to the disappearance, at the beginning of the decompression, of the positive residual pressure due to the jets of respiratory gas.

The positive residual pressure disappears rapidly under the action of the decompression, during the progressive entry of the intake external air. Hence, the positive residual pressure no longer constitutes an obstacle to the intake of external air and to the blood circulation of the person in cardiac arrest.

The variation of intrathoracic pressure between a compression and a decompression, obtained according to the invention, is extended in comparison with the variations of intrathoracic pressure observed in persons under resuscitation, equipped with a known artificial respiration device, for example of the type described by the patent application EP-0911051. The surface of gas exchange is then increased and the venous return is improved. These phenomena are notably explained by application of the inert body physics to the body of the person under resuscitation. By way of illustrative example, the intrathoracic pressure may reach 15 cm of water, during a compression, and −7 cm of water, during a decompression.

Moreover, the local narrowing is devoid of movable element (qui simplify the fabrication thereof) and has constant shape and arrangement, whether a compression or a decompression is exerted on the thoracic cage of the person in state of cardiac arrest. In other words, the local narrowing forms a static and passive gas slow-down means, devoid of inertia.

Moreover, the device of the invention, once connected to the respiratory system of the person in state of cardiac arrest, forms an open system that prevents the appearance of overpressure in the stomach (in other words, any "stomach inflation" is avoided) and allows a continuous supply of respiratory gas while applying, without interruption, alternated compressions and decompressions on the thoracic cage of said person. This reduces the risk of trauma of the respiratory system of the latter, while improving the hemodynamics.

Preferably, said local narrowing may be arranged:

either downstream from said oblong pressure area;
or upstream from said oblong pressure area.

When the device of the invention includes two local narrowings, these latter may be arranged upstream and downstream, respectively.

Preferably, said local narrowing forms a narrowing of the internal section of the tubular element and is an integral part of said device.

As a variant, the device of the invention may include a removable tubular body, in which is arranged said local narrowing forming a narrowing of the internal section of said tubular body.

Furthermore, the device of the invention may include ambient air intake means, for example of the Venturi effect type, which are driven by gas circulating in said main channel.

The present invention also relates to a laryngeal mask comprising an artificial respiration device of the type specified above.

BRIEF DESCRIPTION OF THE DRAWINGS

The figures of the appended drawing will allow a good understanding of how the invention may be implemented. In these figures, same references designate similar elements.

FIGS. 2 and 3 are cross-sectional views of the artificial respiration device of FIG. 1, taken along the lines II-II and III-III respectively.

FIG. 4 is a schematic view, in longitudinal section, of a laryngeal mask provided with a second embodiment of the artificial respiration device according to the invention.

DETAILED DESCRIPTION OF THE PREFERRED EMBODIMENTS

Figure 1:
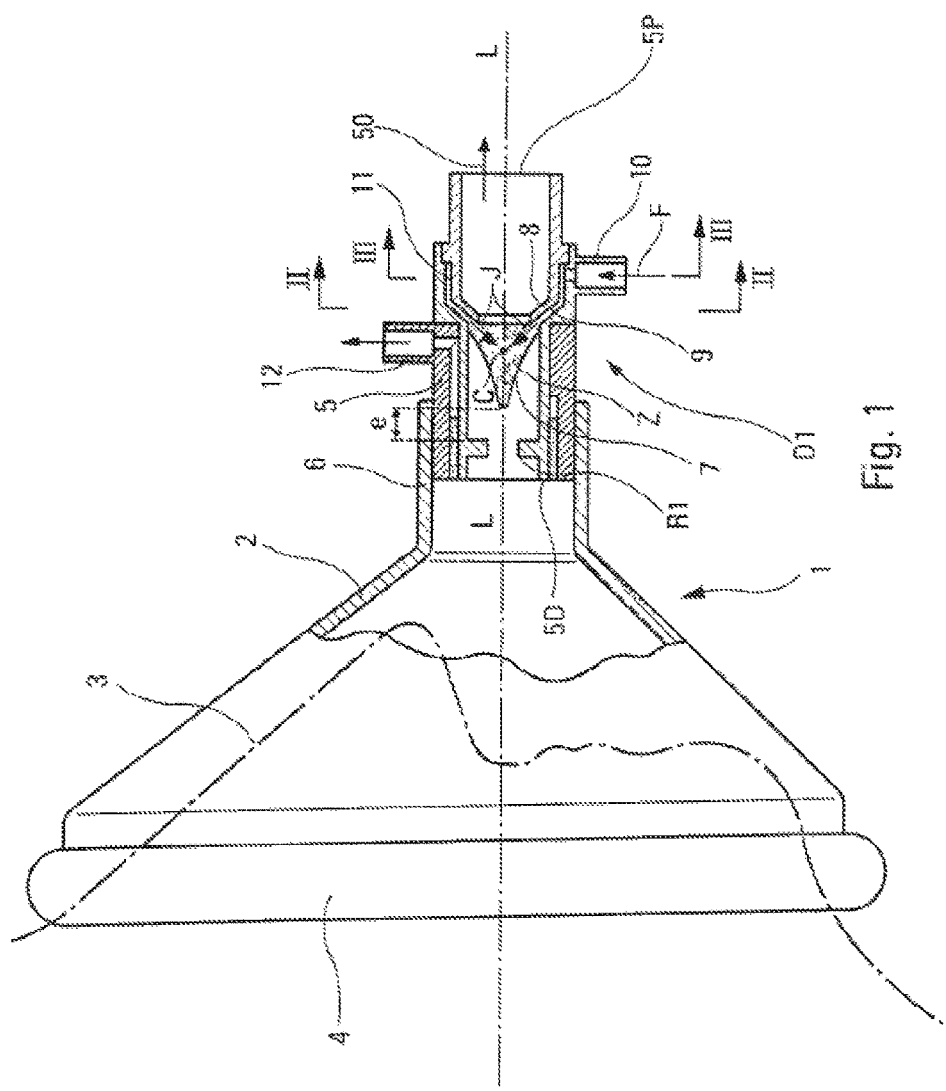
FIG. 1 is a schematic view, in partial axial section, of abucconasal respiratory mask equipped with a first embodiment of the artificial respiration device according to the present invention.

The bucconasal respiratory mask 1, shown in FIG. 1, includes a generally truncated rigid shell 2, which can be applied to the face of a person 3 through a pad 4, lining the peripheral opening thereof. On the opposite side, said mask 1 is provided with an artificial respiration device D1 including a rigid tubular element 5, integral with said shell 2 or fitted into a tubular protruding 6 of the latter. The tubular element 5 serves as a gas entrance and exit tip into and out of the mask 1, its proximal end 5P being on the side of the open air, whereas its distal end 5D is on the side of the mask 1.

The tubular element 5 forms an internal main channel 7 and includes, in the median part, deflection means 8, directed toward the longitudinal axis L-L of said channel 7. The deflection means 8 have for object to deflect, toward said axis of the main channel 7, jets of respiratory gas J injected through peripheral auxiliary channels 9, supplied from a supply tip 10 (see the arrow F symbolizing the respiratory gas supply), through a peripheral annular chamber 11. Said respiratory gas jets thus converge toward a point of convergence C of the axis L-L of said main channel 7 (see also FIGS. 2 and 3). An oblong-shaped pressure area Z is formed, which originates at the distal end of said auxiliary channels 9 and elongates in the distal direction, along the longitudinal axis L-L of the main channel 7.

Moreover, the tubular element 5 includes a tip 12 for gas tapping and/or measurement of pressure.

In the embodiment illustrated in FIG. 4, the laryngeal mask ML is equipped with an artificial respiration device D2 including a flexible tubular element 25, whose distal end 25D is intended to be introduced into a respiratory tract of a patient, whereas the proximal end 25P of the element 25 remains external to said patient. The tubular element 25 forms an internal main channel 27 and includes deflection means 28, directed toward the axis L-L of said channel 27. The deflection means 28 have for object to deflect, toward said axis L-L, jets of respiratory gas J injected through peripheral auxiliary channels 29, supplied from a supply duct 30 (see arrow F), through a peripheral chamber 31, said jets of respiratory gas J converging toward a point of convergence C of said axis L-L. In the same manner as for D1, an oblong-shaped pressure area Z is formed.

The laryngeal mask ML includes a silicone pad 32 with an inflatable cuff, which lines the periphery of the open distal end 25D.

In particular, when they are used for the emergency resuscitation of persons in cardiac arrest, whose thoracic cage is subjected to alternated compressions and decompressions, the artificial respiration devices D1 or D2 are continuously supplied with respiratory gas (arrow F) from pressurized gas cylinders or the like, and the jets J are continuous during the whole process of resuscitation. Generally, the medical gas cylinders deliver the gas under a nominal pressure of the order of 3.5 bars ($3.5 \times 10^5$ Pascal), with a flow rate whose variations are restricted and known.

According to the invention, each of the devices D1 and D2 includes a local narrowing R1, R2 of the internal section of the tubular element 5, 25, which is in the form of a rigid protruding internal ring arranged inside the main channel 7, 27. Such a local narrowing R1, R2 is an integral part of the corresponding devices D1, D2.

In the example of FIG. 1, the local narrowing R1 of the internal section of the main channel 7 of the device D1 is arranged downstream from the oblong pressure area Z, inside said main channel 7.

This local narrowing R1 is longitudinally remote from and external to the pressure area Z. There exists a gap e between the distal end of the pressure area Z and the plane transverse to the axis L-L in which is arranged the narrowing R1.

The manufacturing of the device D1 of the present invention is made, for example, taking into account parameters (pressure, flow rate) specific to the gas cylinders or the like, so that the local narrowing of section R1 is remote from and external to the oblong pressure area Z.

In the example of FIG. 4, the local narrowing R2 of the internal section of the main channel 7 of D2 is positioned upstream from the oblong pressure area Z, inside said main channel 27.

More precisely, the local narrowing R2 is located in the vicinity of the proximal end 25P of the tubular element 25, in such a manner that it is longitudinally remote and distant from the pressure area Z.

During a compression of the thoracic cage of the person 3 equipped with the device D1, D2, the local resistance caused by each of the narrowings R1, R2 generates a pressure increase in the lungs of the person 3, the air expelled from these latter (symbolized by the arrow 50 in FIGS. 1 and 4) escaping freely but with more difficulty.

Conversely, during a decompression of the thoracic cage of said person 3, the pressure decreases more in the lungs than when the devices D1 and D2 are used without local narrowing, so that the variation of intrathoracic pressure between a compression and a decompression increases, which improves the external air pumping effect. The air entry slow-down during a decompression, generated by the narrowings R1 and R2, allows a progressive and controlled intake of the external air toward the lungs of the person, which leads to the disappearance, at the beginning of the decompression, of the positive residual pressure due to the jets J.

Whether it is during a compression or a decompression, the main channel 7, 27 remains open.

Moreover, in the case of the bucconasal mask of FIG. 1, the variation of pressure at the mouth is almost nonexistent.

Furthermore, the supply of the peripheral auxiliary channels 9, 29 of the devices D1, D2 of the invention with respiratory gas (arrow F), from the supply tips 10, 30, may be controlled by means of an electronic valve (not shown), for example operated by an operator.

In particular, such an electronic valve allows, once the heart operation and the blood circulation restored, to switch from a continuous supply of the auxiliary channels 9, 29 with respiratory gas to a pulsed supply, of predefined frequency.

Figure 5:
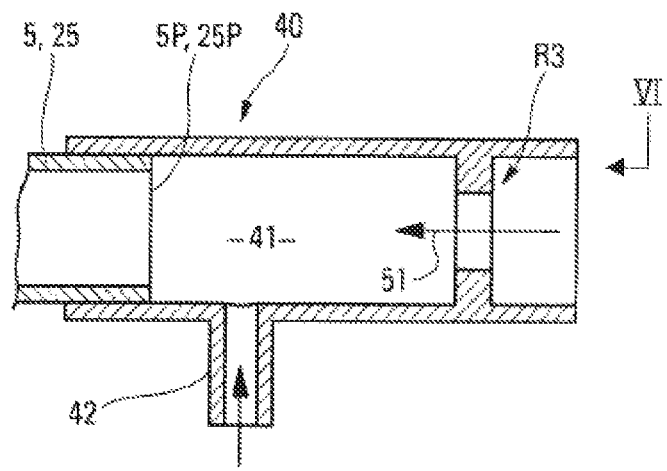
FIG. 5 schematically illustrates, in section, a variant embodiment of the examples of FIGS. 1 and 4 of the device according to the present invention.

Besides, in a variant embodiment shown in FIG. 5, each device D1, D2 may include a tubular body 40 delimiting a cavity 41 in free gaseous communication with the tubular element 5, 25. The tubular body 40 may be removably added on the corresponding device D1, D2, at the proximal end 5P, 25P of the tubular element 5, 25 of the latter.

Inside the tubular body 40 is arranged a local narrowing R3 of the internal section of said body 40.

It will be noted that such a tubular body 40 may be added on the proximal end of the devices D1, D2, whether these latter include, or not, a local narrowing of the internal section of the corresponding tubular element.

Moreover, as schematically shown in FIG. 5, the tubular body 40 includes ambient air intake means 42, of the Venturi effect type, which are driven by gas circulating in the main channel 7, 27 (for example, external air, symbolized by the arrow 51) during a decompression of the thoracic cage of the person under resuscitation.

Figure 6:
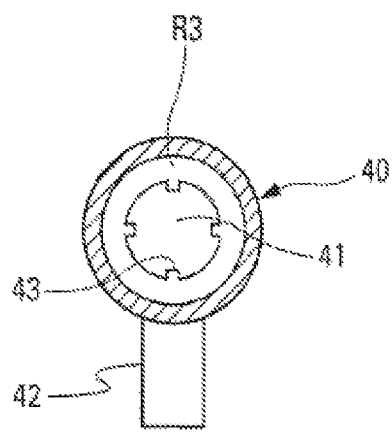
FIG. 6 is a schematic view according to the arrow VI of the removable tubular body of the device according to the invention of FIG. 5.

Furthermore, as illustrated by FIG. 6, the rigid protruding internal ring R3, forming the local narrowing, includes obstacles 43, for example converging wings, inhibiting the accidental introduction of an object liable to hermetically seal the tubular body 40. Such obstacles 43 may also be mounted on the narrowings R1 and R3.

Moreover, the tubular body 40 may include a protruding lateral connection tip (not shown in the Figures), in fluidic communication with the cavity 41, to connect an insufflator balloon to the tubular body 40.

It is to be noted that the device of the present invention is not exclusively intended to be implemented with a bucconasal mask or a laryngeal mask, but could be, for example, integrated to an intratracheal catheter.

The invention claimed is:

1. An artificial respiration device forming an open system configured to provide resuscitation of a person in cardiac arrest, the person having a respiratory system with lungs in a thoracic cage, alternated phased compressions and decompressions being exerted on the thoracic cage, the artificial respiration device comprising:

a tubular element defining at least a portion of a main channel, the tubular element having a proximal end and a distal end and being configured to be connected by the distal end to a respiratory tract of said person, the main channel defining an internal section of the tubular element, the proximal end of said tubular element being external to said person and the respiratory system of the person being connected to outside through said main channel;

a removable tubular body removably connected to the proximal end of the tubular element and forming at least another portion of the main channel in a connected state with the tubular element;

peripheral auxiliary channels that open out into said main channel, said auxiliary channels being continuously supplied with respiratory gas;

a deflection system causing jets of respiratory gas continuously injected by said auxiliary channels to converge toward each other inside the main channel so that an oblong-shaped pressure area originates at a distal end of said auxiliary channels and elongates in the distal direction to a point of convergence of the oblong-shaped pressure area, along the longitudinal axis of said main channel; and a first permanent local section narrowing disposed downstream from the oblong pressure area and a second permanent local section narrowing disposed upstream from the oblong pressure area, the second permanent local section narrowing being disposed in the removable tubular body and forming a narrowing of an internal section of said removable tubular body, each of the first and second permanent local section narrowings being of constant shape and arrangement, to form a local resistance on a gas flow flowing through said main channel, irrespective of the flow direction thereof, each of the first and second permanent local section narrowings being a rigid protruding internal ring protruding internally into the main channel and defining a central opening therethrough, the first and second permanent local section narrowings being longitudinally remote from and external to said oblong pressure area including the point of convergence, the first and second permanent local section narrowings creating an increase of pressure inside the lungs during a compression of the thoracic cage and a decrease of pressure inside the lungs during decompression, wherein the main channel has a first channel width on both sides of each of the protruding internal rings that is greater than a second channel width through the central opening of the respective ring, such that air expelled from the respiratory system of the person and that enters the main channel at the first channel width is restricted within the central opening to cause the local resistance on the gas flow in at least the outward-flowing direction, and the point of convergence of the oblong pressure area being separate from the first and second permanent local section narrowings.

2. The artificial respiration device according to claim 1, wherein the first local section narrowing forms a narrowing of the internal section of the tubular element and is an integral part of said device.

3. A laryngeal mask, comprising:
the artificial respiration device according to claim 2.

4. The artificial respiration device according to claim 2, further comprising ambient air intake means driven by gas circulating in said main channel.

5. The artificial respiration device according to claim 1, wherein the removable tubular body includes an ambient air intake means driven by gas circulating in said main channel and located downstream of the second permanent local section narrowing, the ambient air intake means being a Venture-effect type.

6. A laryngeal mask, comprising:
the artificial respiration device according to claim 1.

7. The artificial respiration device according to claim 1, further comprising ambient air intake means driven by gas circulating in said main channel.

8. The artificial respiration device according to claim 1, wherein the increase of pressure inside the lungs during the compression of the thoracic cage and the decrease of pressure inside the lungs during decompression extends the variation of intra-thoracic pressure between the compression and the decompression in comparison to the absence of the first and second permanent local section narrowings.

* * * * *